United States Patent [19]

Lehman et al.

[11] Patent Number: 4,742,158
[45] Date of Patent: May 3, 1988

[54] PURIFICATION OF HEPATITIS PRE-S ANTIGENS BY POLYMERIZED SERUM ALBUMIN AFFINITY BINDING

[75] Inventors: E. Dale Lehman, Lansdale; Ted F. Schaefer, Collegeville; William J. McAleer, Ambler, all of Pa.

[73] Assignee: Merck & Co., Inc., Rahway, N.J.

[21] Appl. No.: 45,792

[22] Filed: Apr. 14, 1987

Related U.S. Application Data

[63] Continuation of Ser. No. 896,325, Apr. 25, 1986, abandoned.

[51] Int. Cl.$^4$ .......................... C07K 3/20; C07K 3/28; A61K 39/29
[52] U.S. Cl. ...................................... 530/371; 424/88; 435/68; 435/240.27; 530/350; 530/380; 530/413; 530/806; 530/808; 530/826
[58] Field of Search ..................... 424/88; 435/68, 240; 530/350, 371, 808, 826

[56] References Cited

U.S. PATENT DOCUMENTS

| | | | |
|---|---|---|---|
| 4,416,986 | 11/1983 | Markus et al. | 435/68 |
| 4,558,011 | 12/1985 | Brzosko et al. | 530/380 X |
| 4,649,192 | 3/1987 | van Wijnendaele et al. | 530/371 |
| 4,683,293 | 7/1987 | Craig | 530/371 X |
| 4,683,294 | 7/1987 | van Wijnendaele et al. | 530/371 |

FOREIGN PATENT DOCUMENTS 0171908  2/1986  European Pat. Off. .

OTHER PUBLICATIONS

Burnette, Anal. Biochem. 112: 195–203 (1981).
Carty et al., Eighty-Fourth ASM Meeting, p. 194 (1984).
Hilleman et al., Am. J. Med. Sci. 270: 401–407 (1975).
Laemmli, Nature 227: 680–685 (1970).
Machida et a., Gastroentero. 85: 268–274 (1983).
Morrisey, Anal. Biochem. 117: 307–310 (1981).
Neurath and Strick, Arch. Virol. 60: 79–81 (1979).
Valenzuela et al., Bio/Technology 3: 317:320 (1985).

Primary Examiner—Howard E. Schain
Attorney, Agent, or Firm—Jack L. Tribble; Raymond M. Speer; Donald J. Perrella

[57] ABSTRACT

Recombinant pre-S-HBsAg is purified by a rapid and efficient two step chromatographic process. Yeast cells expressing recobinant pre-S-HBsAg are disrupted, the cell contents are clarified and separated by polymerized human serum albumin affinity chromatography. The pre-S-HBsAg is further purified by hydrophobic interaction chromatography using butyl agarose. This process results in pre-S-HBsAg that is greater than 90% pure.

9 Claims, No Drawings

PURIFICATION OF HEPATITIS PRE-S ANTIGENS BY POLYMERIZED SERUM ALBUMIN AFFINITY BINDING

This is a continuation of application Ser. No. 856,325, filed Apr. 25, 1986, now abandoned.

BACKGROUND OF THE INVENTION

The present invention relates to a rapid and efficient method for the purification of yeast expressed recombinant pre-S-Hepatitis B surface antigen (HBsAg).

The hepatitis B pre-S region of the surface antigen has been identified as the receptor site on the virus which binds to hepatocytes prior to entry of the hepatitis B virus into the cell, Valenzuela et al., Bio/Technology 3:317-320 (1985). The pre-S region binds to polymerized serum albumin believed to be associated with the cell membrane of the hepatocytes. Consequently, pre-S containing, recombinant derived, antigens have been suggested as antigens that could induce antibody that would block attachment of the hepatitis B virus to susceptible host cells. Hepatitis B virus pre-S containing surface antigen has been isolated from infected human plasma, Neurath and Strick, Arch. Virol. 60:79-81 (1979) and has recently been obtained using standard recombinant techniques as described by Valenzuela, supra. Indeed, Neurath and Strick were able to isolate a minor population of HBsAg from HBeAg positive human sera by the selective binding to polymerized human serum albumin. The HBsAg was eluted from agarose linked polymerized human serum albumin with 3M sodium thiocyanate. This allowed a 25 to 80-fold purification of the serum HBsAg. This procedure does not, however, allow the purification of recombinant derived pre-S(2)-HBsAg.

SUMMARY OF THE INVENTION

Recombinant pre-S-HBsAg is purified by a rapid and efficient two step chromatographic process. Yeast cells expressing recombinant pre-S-HBsAg are disrupted, the cell contents are clarified and separated by polymerized human serum albumin affinity chromatography. The pre-S-HBsAg is further purified by hydrophobic interaction chromatography using butyl agarose. This process results in pre-S-HBsAg that is greater than 90% pure.

OBJECTS OF THE INVENTION

It is, accordingly, an object of the present invention to provide an efficient procedure for the purification of recombinant derived pre-S-HBsAg. Another object is to provide a method which permits rapid recovery of the pre-S-HBsAg in higher purity and greater yield. These and other objects of the present invention will be apparent from the following description.

DETAILED DESCRIPTION

The present invention relates to a rapid two-step process for isolating pre-S antigens from lysates of yeast cells in which the peptide is produced by recombinant technology. While the following description and examples illustrate the present invention with respect to pre-S(2)-HBsAg, it is to be understood that the present invention is applicable to any protein containing peptides associated with the pre-S region of the hepatitis B surface antigen. Examples include recombinant derived pre-S(1)S(2)-HBsAg, the pre-S(1)S(2) and the pre-S(2) polypeptides which are not covalently bound to the S region of the hepatitis B virus surface antigen.

The recombinant yeast expressing pre-S(2)-HBsAg was obtained using standard recombinant techniques as described by Valenzuela et al., Bio/Technology, 3:317-320 (1985). Yeast cells expressing pre-S(2)-HBsAg are grown by the method of Carty et al., Eighty-Fourth ASM Meeting p. 194, 1984. The cells are harvested, centrifuged and resuspended in a hypertonic buffer consisting of about 0.1 M sodium phosphate, about pH 7.2, and about 0.5M NaCl to a concentration of about 50% (wt./wt.) and stored at about $-70°$ C. The cells are thawed at about 20° to about 23° C., centrifuged and resuspended in Breaking buffer consisting of about 0.1M N-2-Hydroxy-Ethylpiperazine-N'-2-Ethanesulfonic Acid (HEPES) at about pH 7.5 supplemented, with about 0.01M Ethylenediamine-tetraacetic acid (EDTA), about 1 $\mu$g/ml pepstatin A, about 0.13 units/ml aprotinin, about 0.01M benzamidine-HCl and about 2 mM phenylmethane-sulfonic acid (PMSF). The mixture is passed about 1 to about 7 times through a Stansted press to disrupt the cells. The disrupted cell slurry is clarified by centrifugation at about 8,000$\times$g for about 45 minutes at about 4° C.

The clarified yeast extract is added to a column containing Sepharose 4B (Pharmacia) coupled to polymerized human serum albumin (pHSA). Human serum albumin was polymerized with glutaraldehyde as described by Machida et al., Gastroent. 85:268-274 (1983), and coupled to CNBr-activated Sepharose 4B as described by the manufacturer. Following a wash with an acceptable eluant and a wash with Buffer A consisting of about 50 mM HEPES, about pH 7.5 and about 0.5M NaCl the yeast extract is added to the column. An acceptable eluant includes an alkali metal salt of mono-, di- or trihalogenated acetic acid. The alkali metal is lithium, sodium or potassium with sodium being preferred. The halogen is fluorine, chlorine, bromine or iodine with chlorine being preferred. Therefore, the preferred eluant is sodium trichloroacetate. When all of the sample has entered the column the unabsorbed proteins are washed from the column with buffer A. The absorbed pre-S(2)-HBsAg is eluted from the pHSA Sepharose with sodium trichloroacetate in water, about 1 M to about 3.5M, with 3M being preferred, at about pH 6 to about pH 8, with pH 7 being preferred. The pHSA affinity separation resulted in a 80 fold enrichment of the pre-S(2)-HBsAg. Protein blots and silver-stained polyacrylamide gels identified the isolated fraction as re-S(2)-HBsAg and showed a purity of at least 50%.

The Pre-S(2)-HBsAg is further purified by butyl Sepharose (Pharmacia) chromatography. The partially purified pre-S(2)-HBsAg is dialyzed against about 50 mM 3-(N-Morpholino) propane sulfonic acid (MOPS) at about pH 7.0 and pumped onto a butyl Sepharose 4B column. The column is washed and the bound pre-S(2)-HBsAg eluted with about 0.1% Triton X-100 in about 50 mM MOPS at about pH7. The eluted pre-S(2)-HBsAg fraction was shown to be greater than 90% pre-S(2)- HBsAg by silver staining and protein blotting of polyacrylamide gels.

The following examples illustrate the present invention without, however, limiting the same thereto.

EXAMPLE 1

Purification of pre-(S)-HBsAg by Polymerized Human Serum Albumin Affinity Chromatography Recombinant derived yeast expressing pre-S(2)-HBsAg were obtained using standard recombinant techniques as described by Valenzuela et al., Bio/Technology 3:317–320, 1985. Cells were grown as described by Carty et. al., Eighty-Fourth ASM Meeting, 1984, Abstr. 030, p. 194, harvested by concentration, and diafiltered versus phosphate-buffered saline, 7.2 pH. The cells were collected by centrifugation, resuspended in hypertonic buffer (0.1 M sodium phosphate, pH 7.2 and 0.5M NaCl) and stored as a 50% cell suspension (wt./wt.) at −70° C.

All work was done at 4° C. unless stated otherwise. The frozen cell suspension was thawed at 20° C. until the slurry had the consistency of slush. The cell suspension was transferred to a pre-weighed centrifuge bottle and the cell suspension was agitated until totally thawed. The cells were collected by centrifugation at 8000×g for 45 minutes. The cells were prepared for disruption by mixing 154 gm (wet weight) with 250 ml of a breaking buffer (0.1 M HEPES, pH 7.5, 0.01M EDTA. 1 μg/ml pepstatin A, 0.13 units/ml aprotinin, 0.01M benzamidine-HCl and 2 mM PMSF). The cells were evenly dispersed and then passed through a Stansted press, 80 psig, 10–12 psig back pressure. The disruption was repeated four times and the supernatant fluid collected by centrifugation at 8,000×g for 45 minutes.

Human serum albumin was polymerized with glutaraldehyde as described by Machida et al., Gastroentero. 85:268–74, 1983, and coupled to CNBr-activated Sepharose 4B (Pharmacia) following the manufacturer's instruction. A column of polymerized human serum albumin (pHSA) bound Sepharose, bed volume of 64 ml, was prepared and washed with 300 ml of 3M sodium trichloroacetate, pH 7, followed by 700 ml of Buffer A, consisting of 50 mM HEPES, 0.5M NaCl and a pH of 7.5.

Clarified yeast extract, 440 ml containing 20,520 mg of protein and 129 mg of pre-S(2)-HBsAg was pumped onto the PHSA Sepharose column at a flow rate of 25 ml/hour. When all the sample had entered the column the unabsorbed proteins were washed from the column with buffer A. The pre-S(2)-HBsAg was eluted with 3M sodium trichloroacetate, pH 7. Identification and purity analysis of the Pre S(2)-HBsAg was accomplished by polyacrylamide gel electrophoresis followed by either silver staining or immunoblotting. Duplicate aliquots of the fractions eluted from the pHSA column were incubated 15 minutes at 100° C. in 0.05 ml of a buffer containing 2% sodium dodecylsulfate (SDS), 0.125 M Tris-HCl, pH 6.8, and 100 mM dithiothreitol. Samples were electrophoresed through 12.5% polyacrylamide separating gels for 2.5 hour at 65 mA/gel according to Laemmli, Nature 227,680 (1971). One set of gels was stained with silver nitrate to visualize polypeptides as described by Morrissey, Anal. Biochem. 117, 307–310 (1981). The second set of gels was subjected to immunoblotting, Burnette, Anal. Biochem. 112, 195–203 (1981), using rabbit antiserum prepared by the method of Hilleman, el al. Am J. Med. Sci. 270,401 (1975). The eluted fraction contained 43 mg of protein and 22.1 mg of Pre-S(2)HBsAg, indicating an 80 fold enrichment by this technique.

EXAMPLE 2

Secondary Purification of pre-S-HBsAg

The purified pre-S(2) HBsAg obtained in Example 1, was further purified by column chromatography on butyl Sepharose (Pharmacia). A column of butyl Sepharose 4B was prepared and washed with 500 ml of 50 mM MOPS, PH 7.0 (Buffer B) at a flow rate of 30 ml/hour. Purified pre-S(2)-HBsAg was dialyzed against Buffer B and the dialyzed antigen, 118 ml containing 41.5 mg of protein and 21.3 mg of pre-S(2)-HBsAg was pumped onto the column. The column was washed with Buffer B until all unabsorbed proteins had been removed and the pre-S(2)-HBsAg was eluted with Buffer B containing 0.1% Triton X-100. The absorbed fraction contained 13.5 mg of protein and 25 mg of pre-S(2)-HBsAg. Silver staining and protein blotting of polyacrylamide gels as described in Example 1, revealed that the fraction was greater than 90% pre-S(2)-HBsAg.

What is claimed is:

1. A method of purifying recombinant expressed hepatitis B virus pre-S surface antigens comprising:
   a. attachment of pre-S(2) containing antigen to a polymerized serum albumin matrix;
   b. elution of the antigens from the matrix with a salt formed by an alkali metal and a halogenated acetic acid; and
   c. final purification of the antigens using butyl agarose affinity chromatography and an acceptable eluant.

2. A method according to claim 1, step a, wherein the albumin is human or chimpanzee serum albumin.

3. A method according to claim 1, step a, wherein the albumin is human serum albumin.

4. A method according to claim 1, step a, wherein the antigen is pre-S(2)-HBsAg, pre-S(1)S(2)-HBsAg, pre-S(1)S(2) or pre-S(2).

5. A method according to claim 1, step b, wherein the alkali metal is lithium, sodium or potassium.

6. A method according to claim 4 wherein the alkali metal is sodium.

7. A method according to claim 1, step b, wherein there is one, two or three molecules of the halogen.

8. A method according to claim 1, step b, wherein the halogenated acetic acid contains three molecules of fluorine, chlorine, bromine, or iodine.

9. A method according to claim 1, step b, wherein the alkali metal salt of the halogenated acetic acid is trichloroacetate.

* * * * *